United States Patent [19]

Tsunoda et al.

[11] 4,292,448

[45] Sep. 29, 1981

[54] PROCESS FOR THE HYDROFORMYLATION OF OLEFINS

[75] Inventors: Yoshitoshi Tsunoda; Shimpei Tomita; Chihiro Miyazawa, all of Kurashiki, Japan

[73] Assignee: Mitsubishi Chemical Industries Ltd., Tokyo, Japan

[21] Appl. No.: 142,686

[22] Filed: Apr. 22, 1980

[30] Foreign Application Priority Data

May 11, 1979 [JP] Japan .................................. 54-57862
Jan. 18, 1980 [JP] Japan .................................. 55-4332

[51] Int. Cl.$^3$ ............................................. C07C 45/50
[52] U.S. Cl. .................................... 568/456; 568/454
[58] Field of Search ................................. 568/454, 456

[56] References Cited

U.S. PATENT DOCUMENTS

| | | | |
|---|---|---|---|
| 3,547,964 | 12/1970 | Olivier | 568/456 |
| 3,560,539 | 2/1971 | Booth | 568/456 |
| 3,899,442 | 8/1975 | Friedrich | 568/456 |
| 4,135,911 | 1/1979 | Balmat | 568/456 |

FOREIGN PATENT DOCUMENTS

| | | | |
|---|---|---|---|
| 50-41805 | 4/1975 | Japan | 568/456 |
| 50-71610 | 6/1975 | Japan | 568/456 |
| 51-8207 | 1/1976 | Japan | 568/456 |

*Primary Examiner*—Werren B. Lone
*Attorney, Agent, or Firm*—George Loud

[57] ABSTRACT

A process for the hydroformylation of an olefin, comprising reacting the olefin with carbon monoxide and hydrogen in a catalyst liquid containing a Group VIII noble metal-triarylphosphine complex catalyst, excess triarylphosphine and a reaction solvent to form an aldehyde, characterized by withdrawing a part of the catalyst liquid as a spent catalyst liquid, subjecting the spent catalyst liquid to crystallization, recovering crystallized triarylphosphine from the spent catalyst liquid, and recirculating the recovered triarylphosphine into the reaction zone.

15 Claims, No Drawings

PROCESS FOR THE HYDROFORMYLATION OF OLEFINS

BACKGROUND OF THE INVENTION

1. Field of the Invention

This invention relates to a process for the hydroformylation of olefins.

More particularly, this invention relates to a hydroformylation process for separating and recovering triarylphosphine selectively from a liquid reaction product of the hydroformylation of olefins containing a Group VIII noble metal-triarylphosphine complex catalyst, free triarylphosphine, by-product triarylphosphine oxide, formed aldehyde and a reaction solvent, and recirculating it into a hydroformylation reaction zone.

2. Description of the Prior Art

It is well known that Group VIII noble metal-triarylphosphine complex catalyst, particularly Group VIII noble metal-triphenylphosphine complex catalysts, and more particularly, rhodium-triphenylphosphine complex catalyst are advantageous for industrial use as catalysts for the hydroformylation reaction in which an olefin is hydroformylated to form an aldehyde having one more carbon atom than the olefin. Group VIII noble metal-triarylphosphine complex catalysts, with which free triarylphosphine should preferably coexist, provide great advantages because of their high thermal stability, as follows:

(1) After the aldehyde formed is separated by distillation, gas blow stripping, or otherwise from a liquid product of the hydroformylation reaction containing the complex catalyst, the residue containing the complex catalyst can be recirculated into a hydroformylation reaction zone; and (2) While the aldehyde formed is being separated from the reaction zone in gaseous form with the unreacted gas, by reactive distillation, for example, stripping with unreacted gas containing olefin, carbon monoxide and hydrogen, from the liquid product of hydroformylation containing the complex catalyst, or otherwise, the hydroformylation can be continued with the catalyst liquid containing the complex catalyst remaining in the reaction zone. In this case, the aldehyde condensation by-product having a high boiling point can be removed simultaneously (Japanese Laid-Open Patent Application No. 125103/1977).

The recirculation of Group VIII noble metal-triarylphosphine complex catalyst for reuse, or the continued use thereof in the reaction zone as described above is very advantageous, but nevertheless, presents the following problems which everybody engaged in the hydroformylation of olefins with such catalysts desires to solve:

The recirculation of a catalyst liquid containing a Group VIII noble metal-triarylphosphine complex catalyst, free triarylphosphine, etc. for reuse in an industrial process results in the collection in the catalyst liquid of a by-product formed mainly by secondary reactions of the aldehyde formed, and having a higher boiling point than the aldehyde, triarylphosphine oxide formed by oxidation of a part of triarylphosphine with oxygen dissolved in the solvent, present in the raw materials, or mixing into the process line during various steps of operation, or the like. In the event the catalyst liquid is continuously used in the reaction zone while the aldehyde formed is being separated therefrom by reactive distillation, etc., triarylphosphine oxide formed as described above, or the like collects in the catalyst liquid in the reaction zone, though the high-boiling aldehyde condensation by-product can be removed.

The accumulation of the high-boiling by-product, triarylphosphine oxide, etc., as described above leads to a corresponding increase in the volume of the catalyst liquid as a whole, and ultimately disables a reaction vessel having a fixed capacity to continue operation. Particularly, it is known that if triphenylphosphine is employed as triarylphosphine, the accumulation of triphenylphosphine oxide formed by oxidation of triphenylphosphine causes an undesirable increase in the formation of branched aldehyde and adversely affect the rate of the reaction (Japanese Laid-Open Patent Application No. 8207/1976).

The reuse of the catalyst liquid by recirculation or the continued use thereof over a long period of time leads to reduction in the activity of the catalyst. With the accumulation of reaction time, the catalyst deactivated by reaction inhibitors contained in minor quantities in the raw materials collects in the catalyst liquid, and the catalyst liquid has a gradually decreasing catalytic activity until it finally finds it difficult to maintain a desired rate of reaction.

These problems of the accumulation of the high-boiling by-product, triarylphosphine oxide and deactivated catalyst can be solved by removing a part of the recirculated catalyst liquid containing such substances uniformly, or a part of such catalyst liquid in the reaction zone continuously or intermittently from the reaction system, and replenishing the reaction zone with a corresponding quantity of an active Group VIII noble metal-triarylphosphine complex, or a rhodium salt as a source of such complex, and free triarylphosphine, and if required, a reaction solvent. This method makes it possible to maintain the concentration of each of the substances accumulated in the catalyst liquid being recirculated or remaining in the reaction zone at an equilibrium level which depends on the amount of the catalyst liquid removed and the amount of each such substance formed, thereby permitting stabilized operation of the reaction vessel for hydroformylation with a fixed concentration of such substances. The aforementioned equilibrium concentration is determined at an optimum level which is required on an industrial basis.

The catalyst liquid removed from the reaction system (hereinafter referred to as the spent catalyst liquid) contains useful and expensive triarylphosphine and Group VIII noble metal forming a complex therewith. It is, thus, very desirable from an industrial standpoint to recover and reuse such triarylphosphine and noble metal efficiently.

Various methods have hitherto been proposed for recovering Group VIII noble metals from the spent catalyst liquid. They include adsorption (Japanese Patent Publication No. 28273/1973, Japanese Laid-Open Patent Application No. 7114/1972, etc.), extraction with a strong acid (Japanese Patent Publication No. 43219/1971), and combustion (Japanese Laid-Open Patent Application No. 39690/1975).

On the other hand, only two methods are known for recovery of triarylphosphine, particularly triphenylphosphine, i.e., extraction with a strong mineral acid (Japanese Patent Publication No. 43219/1971), and extraction with formaldehyde-strong mineral acid (West German OLS 25 02 233). According to the former method, rhodium is extracted simultaneously with free triphenylphosphine, and the latter method also extracts free triphenylphosphine in aqueous layer with rhodium. In any event, as triphenylphosphine is extracted as a salt in the aqueous layer, it must be neutralized with an alkali for removal of counter ions such as sulfate ions ($SO_4^{--}$) and chloride ion ($Cl^-$), so that it can be recirculated into the reaction zone for hydroformylation. As chlorine (Cl), sulfur (S), etc. are known to be poisonous to a rhodium catalyst (Japanese Laid-Open Patent Application Nos. 41805/1975 and 71610/1975), and can also cause corrosion to the reaction vessel, the triphenylphosphine recovered by these methods requires careful removal of those anions and purification prior to recirculation for reuse.

The inventors of this invention have made an extensive study as to any possible method for recovering triarylphosphine selectively from the spent catalyst liquid without involving any chloride or sulfate ion, or the like, that may be poisonous to the catalyst, or cause corrosion to the reaction vessel. As the result, the inventors have discovered that triarylphosphine, triarylphosphine oxide and Group VIII noble metal-triarylphospnine complex catalyst have different degrees of solubility in the high-boiling by-products of hydroformylation to the extent which is appropriate for the selective separation of triarylphosphine. This invention is based on such discovery.

SUMMARY OF THE INVENTION

It is an object of this invention to provide an industrially advantageous process for hydroformylation of olefins.

It is another object of this invention to provide a process for hydroformylation of olefins which facilitates selective recovery of useful and expensive triarylphosphine with a high yield, and recirculation thereof into the reaction zone for reuse in hydroformylation.

It is still another object of this invention to provide a process for hydroformylation of olefins in which triarylphosphine oxides which inhibit the catalytic action can be selectively removed simultaneously with the recovery of triarylphosphine.

According to this invention there is provided a process for the hydroformylation of an olefin comprising reacting the olefin with carbon monoxide and hydrogen in a catalyst liquid containing a Group VIII noble metal-triarylphosphine complex as a catalyst, excess triarylphosphine and a reaction solvent in a reaction zone to thereby form an aldehyde, and separating said aldehyde by evaporation from said reaction zone or by distillation in a separating step, the improvement which comprises removing a part of said catalyst liquid from said reaction zone or said separating step as a spent catalyst liquid, subjecting said spent catalyst liquid to crystallization, recovering crystallized triarylphosphine from said spent catalyst liquid, and recirculating said recovered triarylphosphine into said reaction zone.

DETAILED DESCRIPTION OF THE INVENTION

This invention is applicable to the selective recovery of triarylphosphine from the spent catalyst liquid leaving the reaction zone, and the reuse of such triarylphosphine in the reaction zone for the hydroformylation of olefins with a Group VIII noble metal-triarylphosphine complex catalyst in the presence of excess triarylphosphine.

The olefins to be hydroformylated include hydrocarbons having at least one olefinically unsaturated bond, particularly linear or branched lower olefins. It is preferable to use linear α-olefins having two or more carbon atoms, such as ethylene, propylene, 1-butene and 1-hexene, while it is also possible to use inner olefins, such as 2-butene, 2-pentene and 2-hexene.

It is equally possible to use olefins having a vinylidene structure, such as isobutene.

A mixed gas of carbon monoxide and hydrogen which is supplied into the reaction vessel is usually called water gas or oxo gas, and typically comprises a molar proportion of $H_2$ to CO of $\frac{1}{3}$ to 20, preferably $\frac{1}{3}$ to 10.

Group VIII noble metal-triarylphosphine complex catalyst used for hydroformylation can be easily prepared by a known method of forming a complex from compounds of Group VIII noble metals, such as hydrides, halides, carboxylates, nitrates and sulfates, and triarylphosphine. These Group VIII noble metal compounds and triarylphosphine may form a complex before introduction into the reaction zone, or alternatively, they can be separately supplied into the reaction zone to form a complex therein.

For triarylphosphine as a ligand, it is most desirable to use triphenylphosphine, but it is also possible to use triarylphosphine having its phenyl group substituted by a methyl or other lower alkyl group, such as tri-p-tolylphosphine, tri-m-tolylphosphine, trixylylphosphine and tris(p-ethylphenyl) phosphine; triarylphosphine having its phenyl group substituted by a methoxy or other alkoxy group, such as tris(p-methoxyphenyl) phosphine, or any other triarylphosphine having bonded thereto a substituent which is inert under the hydroformylation conditions.

Specific examples of Group VIII noble metal compounds used for preparing a complex include ruthenium compounds, such as ruthenium trichloride and ruthenium tetraaminehydroxochloro chloride; rhodium compounds, such as rhodium dicarbonylchloride, rhodium nitrate, rhodium trichloride, rhodium acetate and rhodium sulfate; palladium compounds, such as palladium hydride, palladium chloride, palladium iodide, palladium nitrate, palladium cyanide, palladium acetate and palladium sulfate; osmium compounds, such as osmium trichloride and chloroosmic acid; iridium compounds, such as iridium tribromide, iridium tetrabromide, iridium trifluoride, iridium trichloride and iridium carbonyl; and platinum compounds, such as platinic acid, platinous iodide, sodium hexachloroplatinate and potassium trichloro-monoethyleneplatinate. As is well known to those skilled in the art, tertiary phosphines, such as triarylphosphine, are usually applied to coexist in the reaction zone in order to increase the thermal stability of the complex catalyst, and the proportion of useful linear aldehyde in the aldehyde formed by the reaction, and the amount of such tertiary phosphine is usually from several tens of to several hundred times greater by molar ratio than that of the complex catalyst in the reaction zone.

According to the process of this invention, the aldehyde formed by the reaction is separated by distillation in the separating step, or evaporation from the reaction zone.

Referring first to the process wherein the recovery of the aldehyde is carried out by distillation in the separating step, an organic solvent which dissolves the raw material and the catalyst, is inert to the reaction for hydroformylation, and does not react with the aldehyde formed, is used as a reaction solvent. Any such solvent having a higher boiling point than the aldehyde is satisfactory, and examples of such solvents include aromatic hydrocarbons such as benzene, toluene and xylene, saturated aliphatic hydrocarbons such as heptane and decane, and esters such as butyl acetate and ethyl butyrate. If desired, the aldehyde per se may be used as such a solvent. In this case, the reaction may usually be carried out at a temperature of 50° to 150° C. and a pressure of 1 to 100 atm, preferably 20 to 100 atm.

According to this method, the reaction is carried out at predetermined temperature and pressure in an ordinary continous reaction vessel fed with the raw materials, i.e., olefin, oxo gas and the constituents of a catalyst liquid, such as a Group VIII noble metal-triarylphosphine complex catalyst, excess triarylphosphine and a reaction solvent, as is well known in the art. The unreacted olefin and the aldehyde formed are separated from the liquid reaction product leaving the reaction vessel by a known method such as distillation, and the catalyst liquid containing the complex is recirculated into the reaction vessel. As already described, a part of the catalyst liquid to be recirculated is removed from the reaction system continuously or intermittently as the spent catalyst liquid in order to avoid accumulation of deactivated catalyst and high-boiling by-products, and corresponding amounts of fresh catalyst and triarylphosphine are supplied into the reaction system to make up for the removal.

Although the process of this invention is applicable directly to the spent catalyst liquid removed from the reaction system, it is usually more advantageous to apply the process of this invention after the solvent is removed from the catalyst liquid by a known method such as distillation to increase the concentration of triarylphosphine in the liquid. The removal of the solvent from the spent catalyst liquid is carried out by ordinary distillation, such as atmospheric or vacuum distillation, or gas blow stripping, or otherwise. Distillation should preferably be conducted so that the solvent content of the spent catalyst liquid is not greater than 20% by weight, preferably not greater than 5% by weight, and more preferably 0%. Thus, the spent catalyst liquid is subjected to crystallization directly or after the solvent is removed as described above.

Referring next to the process wherein the recovery of the aldehyde is carried out by evaporation from the reaction zone, a high-boiling organic compound composed principally of the self-polymerization or condensation product of the aldehyde formed, is usually used as a reaction solvent. It is also possible to use during the beginning of hydroformylation the afore-mentioned organic solvent which is inert to the reaction and separable from the aldehyde by distillation, and replace it during the later period of the reaction with the high-boiling organic compound which is formed as a by-product of the reaction. In this case, the reaction may be carried out at a temperature of 50° to 150° C. and a pressure of 1 to 100 atm.

According to this method, the reaction for hydroformylation is carried out at predetermined temperature and pressure after the raw materials, i.e., olefin and oxo gas, are introduced into the reaction vessel containing a catalyst liquid composed of a Group VIII noble metal-triarylphosphine complex catalyst, excess triarylphosphine, a reaction solvent and if appropriate, the aldehyde formed, as is well known in the art. The aldehyde formed by the reaction is evaporated from the reaction zone by, for example, stripping with an unreacted gas containing unreacted olefin, carbon monoxide, hydrogen, etc. as a gaseous mixture with such unreacted gas, and removed from the reaction vessel. The high-boiling by-product which is simultaneously formed leaves the reaction vessel with the unreacted gas. The amount of the high-boiling by-product leaving the reaction vessel is preferably such that a total of it and the high-boiling by-product discharged with the spent catalyst liquid to be removed from the reaction zone to be described later in further detail may be approximately equal to the amount which is formed. If too much high-boiling by-product leaves with the unreacted gas, a part of the by-product which has flown out is recirculated into the reaction zone to maintain a constant amount of catalyst liquid.

Thus, the amount of the catalyst liquid in the reaction vessel for hydroformylation is maintained constant at a predetermined level. The liquid component consisting mainly of the aldehyde in the gaseous mixture removed from the reaction vessel is separated from the unreacted gas by cooling and condensation, and the unreacted gas, except a small amount thereof which is purged to prevent accumulation of mainly paraffins as hydrogenation by-products, is recirculated into the reaction vessel. As already described, a part of the catalyst liquid in the reaction zone is removed therefrom continuously or intermittently as the spent catalyst liquid in order to avoid accumulation of deactivated catalyst and the high-boiling by-product as the case may be, and those amounts of fresh catalyst and triarylphosphine which are required to make up for the loss are supplied into the reaction zone.

The process of this invention is usually applied to the residue remaining after the aldehyde formed by the reaction is removed from the spent catalyst liquid leaving the reaction system. If the spent catalyst liquid contains a large quantity of reaction solvent other than the high-boiling by-product, however, the process of this invention can be more advantageously utilized after a part of the reaction solvent is removed from the spent catalyst liquid by a known method such as distillation to increase the concentration of triarylphosphine in the liquid. The removal of the solvent from the spent catalyst liquid is performed by ordinary distillation such as atmospheric or vacuum distillation, or gas blow stripping, or otherwise.

The spent catalyst liquid, from which the aldehyde or a part of the solvent is removed as described above, is subjected to crystallization.

The spent catalyst liquid which is subjected to crystallization contains the high-boiling organic compound which is formed as a by-product of the hydroformylation reaction (hereinafter referred to as the "high-boiling organic by-product"). The high-boiling organic by-product is a product of the secondary reaction of the aldehyde formed by the hydroformylation. For example, the hydroformylation of propylene forms n-butyraldehyde and i-butyraldehyde, and these aldehyde products are so highly reactive that even at a relatively low temperature in the absence of any catalyst, they undergo polymerization or condensation to form a high-boiling polycondensation product.

These high-boiling polymerization or condensation products include, for example, the self-polymerization products of n-butyraldehyde, such as a dimer, i.e., an aldol and a trimer (to be hereinafter described), a condensation dimer such as 2-ethylhexenal, and hydrogenation products thereof such as 2-ethylhexanal and 2-ethylhexanol, and other higher boiling polymerization or condensation products. Likewise, i-butyraldehyde forms self-polymerization products such as dimers and trimers by a similar reaction, and i-butyraldehyde and n-butyraldehyde form co-polymerization products such as dimers, trimers and derivatives thereof. The aforementioned high-boiling organic by-products comprise these high-boiling polymerization or condensation products, and other unidentifiable high-boiling substances, and particularly, the hydroformylation of olefins forms larger amount of high-boiling trimeric polymerization products of linear and branched aldehydes formed from the corresponding olefins, having the structures represented by the following general formulas (I) and (II), as compared with any other high-boiling substance:

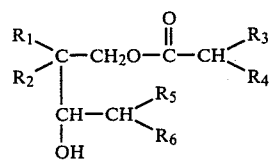
(I)

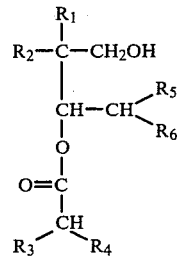
(II)

wherein $R_1$, $R_2$, $R_3$, $R_4$, $R_5$ and $R_6$ each represent hydrogen, or a linear or branched alkyl group having 1 to 6 carbon atoms.

The high-boiling polymerization products having the structures represented by the foregoing formulas (I) and (II) occupy 10 to 100% by weight, usually 30 to 80% by weight of the spent catalyst liquid excluding the Group VIII noble metal-triarylphosphine complex, triarylphosphine and triarylphosphine oxide.

The high-boiling organic by-product is a good solvent having a large power of dissolving Group VIII noble metal-triarylphosphine complex catalyst and triarylphosphine oxide, but has a relatively small power of dissolving triarylphosphine. Particularly, triarylphosphine has a low degree of solubility in the high-boiling polymerization products having the structures shown by the formulas (I) and (II) above.

The process of this invention relies on the different degress of solubility of the complex catalyst, triarylphosphine oxide and triarylphosphine in the high-boiling organic by-products to realize the selective recovery of triarylphosphine by crystallization of the spent catalyst liquid. If desired, it is also possible to conduct the crystallization of the spent catalyst liquid by adding further a known poor solvent for triarylphosphine, such as methanol.

When the spent catalyst liquid is subjected to crystallization, the concentration of triarylphosphine in the liquid depends mainly on the difficulty of the crystallizing operation, but is preferably from 1 to 60% by weight. The concentrations of the Group VIII noble metal-triarylphosphine complex catalyst and triarylphosphine oxide in the spent catalyst liquid are usually in the ranges of 0.001 to 10% by weight and 0 to 50% by weight, respectively, though there is no particular limitation as far as they can be dissolved.

For the crystallization of the spent catalyst liquid, it must contain a specific amount of high-boiling organic by-product relative to triarylphosphine. The crystallization is usually carried out when the triarylphosphine and the high-boiling organic by-product in the spent catalyst liquid have a weight ratio of 1:0.2 to 1:100, preferably 1:0.6 to 1:99.

If the concentration of triarylphosphine in the spent catalyst liquid removed from the hydroformylation system is too low to fall within the aforementioned range, it is desirable to concentrate the liquid by vacuum distillation or otherwise before the crystallization of the liquid. If the concentration of the high-boiling organic by-product in the spent catalyst liquid is too low to fall within the aforementioned range, it is possible to incorporate an additional amount of such high-boiling organic by-product for the crystallization of the liquid.

The crystallization of the spent catalyst liquid can be properly accomplished in a known crystallizing apparatus by single-stage or multistage crystallization, or otherwise. The crystallizating temperature is not particularly limited, as far as the triarylphosphine to be crystallized is separable from the spent catalyst liquid, but is usually from $-78°$ C. to $80°$ C., and preferably from $-20°$ C. to $50°$ C. The triarylphosphine thus crystallized is recovered from the mother liquid by an ordinary method of filtration or centrifugal separation, or otherwise. The crystallization and recovery of triarylphosphine should preferably be carried out in an inert gas atmosphere, such as nitrogen and carbon dioxide, in order to prevent oxidation of triarylphosphine into triarylphosphine oxide in the presence of oxygen.

The triarylphosphine thus recovered is recirculated into the hydroformylation reaction zone for reuse directly or after purification by distillation, recrystallization, or otherwise. For such recirculation, triarylphosphine can be dissolved in the solvent for hydroformylation. For this purpose, it is satisfactory to use the solvent which has been removed by distillation prior to crystallization.

The Group VIII noble metal present in the mother liquid after the recovery of triarylphosphine is recovered therefrom by combustion of the liquid or any other known method for catalyst metal recovery. The noble metal so recovered is reused as a catalyst for hydroformylation after it has undergone the necessary treatment.

It will be understood from the foregoing description that this invention has a very significant industrial value, as the process permits the selective recovery of useful and expensive triarylphosphine with a high yield from the reaction product of hydroformylation by simple methods of distillation, crystallization and solid-liquid separation utilizing the high-boiling by-product of the reaction, thereby making it possible to reuse the recovered triarylphosphine for hydroformylation.

This invention is also of high industrial value, as during the recovery of triarylphosphine, the process makes it possible to remove selectively the triarylphosphine oxide, collecting in the reaction liquid, which is a catalytic action inhibitor reducing the proportion of useful linear aldehyde formed by the reaction.

Moreover, the process of this invention accomplishes the hydroformylation of olefins with significant industrial advantages, since a combination of the recovery of triarylphosphine by the method of this invention and the recovery of Group VIII noble metal by a known method permits the high-yield recovery of high purity triarylphosphine and Group VIII noble metal which are useful and expensive, from the spent catalyst liquid in the hydroformylation system, and the reuse thereof for hydroformylation.

The invention will now be described more specifically with reference to examples, which are not intended in any way to limit this invention unless it departs from the scope and spirit thereof.

Example 1—Recovery of Triphenylphosphine from Spent Catalyst Liquid

Unreacted olefin and formed aldehyde were separated from the liquid reaction product formed by the hydroformylation of propylene in an industrial reaction apparatus in the presence of a rhodium-triphenylphosphine complex catalyst with excess triphenylphosphine to obtain a catalyst liquid to be recirculated into the reaction system. A part of the catalyst liquid thus obtained was removed as the spent catalyst liquid, and toluene used as the solvent was separated from the spent catalyst liquid by an ordinary method of distillation, whereby a distillation residue composed as shown in Table 1 was obtained. One hundred grams of the residue having a temperature of 120° C. was introduced into a four-necked flask provided with a thermometer and a stirrer, filled with nitrogen and having a capacity of 300 ml. The residue was cooled to 10° C. under stirring, and held at that temperature for 60 minutes. Then, the liquid was transferred in a stream of nitrogen into a vessel for centrifugal separation provided with a cooling jacket, and while the interior temperature of the vessel was maintained at 10° C., the vessel was rotated at a speed of 300 to 500 rpm to continue centrifugal separation for 30 minutes, whereby crystals of triphenylphosphine were recovered. Twenty-four grams of triphenylphosphine crystals were recovered with a recovery yield of 80%. Triphenylphosphine could be selectively recovered, as the crystals contained only 0.1 g of triphenylphosphine oxide and 4.5 mg of the rhodium complex based on the weight of the metallic rhodium. The mother liquid remaining after the centrifugal separation contained 6 g of triphenylphosphine, 2.9 g of triphenylphosphine oxide, and 40.5 mg of the rhodium complex based on the weight of the metallic rhodium.

TABLE 1

| Composition of the distillation residue | | |
|---|---|---|
| Constituents | Composition (wt. %) | Content in 100 g of residue (g) |
| Rhodium-triphenylphosphine complex (based on metallic rhodium) | 0.045 | 0.045 |
| Free triphenylphosphine | 30 | 30 |
| Free triphenylphosphine oxide | 3 | 3 |
| High-boiling organic by-products shown by formulas (I) and (II) above *1 | 60 | 60 |
| Other high-boiling organic by-products | 6.6 | 6.6 |

*1 A total of the compounds 'a', 'b' and 'c' represented by the formulas (I) and (II) when $R_1$ through $R_6$ are as shown in Table 2 below.

TABLE 2

| Cpd. | $R_1$ | $R_2$ | $R_3$ | $R_4$ | $R_5$ | $R_6$ | Content (wt. %/residue) |
|---|---|---|---|---|---|---|---|
| a | H | $C_2H_5$ | H | $C_2H_5$ | H | $C_2H_5$ | 18 |
| b | $CH_3$ | $CH_3$ | $CH_3$ | $CH_3$ | $CH_3$ | $CH_3$ | 9 |
| c | H | $C_2H_5$ | H | $C_2H_5$ | $CH_3$ | $CH_3$ | |
|   | H | $C_2H_5$ | $CH_3$ | $CH_3$ | H | $C_2H_5$ | |
|   | $CH_3$ | $CH_3$ | H | $C_2H_5$ | H | $C_2H_5$ | |
|   | H | $C_2H_5$ | $CH_3$ | $CH_3$ | $CH_3$ | $CH_3$ | 33 |
|   | $CH_3$ | $CH_3$ | $CH_3$ | $CH_3$ | H | $C_2H_5$ | |
|   | $CH_3$ | $CH_3$ | H | $C_2H_5$ | $CH_3$ | $CH_3$ | |

Example 2—Hydroformylation of Propylene with Triphenylphosphine Recovered and Purified An autoclave equipped with a magnetic stirrer and having a capacity of 200 ml was fed with 45 ml of toluene, 6 g of the triphenylphosphine*2 recovered in Example 1 and purified by recrystallization from benzene-methanol in a customary manner, and 1.5 mg of rhodium acetate based on the weight of metallic rhodium. The autoclave was purged with nitrogen gas, and fed with 238 m mol of propylene by distillation. The autoclave was heated to 120° C., and a mixed gas consisting of carbon monoxide and hydrogen (oxo gas having a molar ratio of $H_2/CO = 1$) was forced into the autoclave. The reaction was initiated at 120° C. and a constant pressure of 50 kg/cm$^2$G. The autoclave was connected to a high pressure oxo gas holder via a pressure controller, so that it might be replenished with oxo gas to make up for its consumption by the reaction to thereby maintain a constant pressure throughout the reaction. The reaction was deemed to have been completed when the absorption of the gas ceased to be observed, and after the autoclave was cooled, the residual propylene in gaseous and liquid phases, and the butyraldehydes formed by the reaction were analyzed by gas chromatography.

*2—A rhodium analysis confirmed that the triphenylphosphine contained virtually no rhodium complex therein.

According to the results obtained, propylene showed a conversion of 99.6%, and a selectivity of 99.5% for butyraldehydes. The formed butyraldehydes showed a normal/iso ratio of 2.38. A curve showing the decrease of oxo gas pressure in the high pressure gas holder gave a rate constant (first-order reaction) of 1.57 (l/h).

Reference Example 1—Hydroformylation of Propylene with New Triphenylphosphine Never Used for Hydroformylation Before The procedures of Example 2 were repeated, except that the same triphenylphosphine as supplied into the industrial reaction apparatus in Example 1 was used instead of the triphenylphosphine recovered and purified in Example 2.

As the result, propylene showed a conversion of 99.6%, and a selectivity of 99.5% for butyraldehydes. The formed butyraldehydes showed a normal/iso ratio of 2.36. The rate constant (first-order reaction) was 1.55 (l/h).

Example 3—Hydroformylation of Propylene with Triphenylphosphine Not Purified After Recovery The procedures of Example 2 were repeated, except that the triphenylphosphine recovered in Example 1 and containing a very small amount of rhodium complex was used without purification. As the result, propylene showed a conversion of 99.6%, and a selectivity of 99.5% for butyraldehydes. The formed butyraldehydes showed a normal/iso ratio of 2.35, and the rate constant (first-order reaction) was 2.78 (l/h).

Example 4—Correction Experiment for Determining the Reaction Activity of Rhodium Complex Remaining in the Recovered Triphenylphosphine The procedures of Example 3 were repeated, except that no rhodium acetate was used. As the result, propylene showed a conversion of 99.6%, and a selectivity of 99.5% for butyraldehydes. The formed butyraldehydes showed a normal/iso ratio of 2.31. The remaining rhodium complex showed a rate constant (first-order reaction) of 1.20 (l/h.)

The results of Examples 2 to 4, and Reference Example 1 may be summarized as shown in Table 3 below.

TABLE 3

Activity of a rhodium complex catalyst containing 1.5 mg of metallic rhodium as initially added

| | Triphenylphosphine | Presence of rhodium | Rate constant (first-order, 1/h) |
|---|---|---|---|
| Example 2 | Recovered and purified | No | 1.57 |
| Reference Example 1 | Same as used in the industrial reaction apparatus | No | 1.55 |
| Examples 3 and 4 | Recovered, but not purified | Yes | 1.58 (=2.78−1.20) |

Example 5

The procedures of Example 1 were repeated for recovery of triphenylphosphine, except that the temperature of the residue was lowered from 120° C. to 0° C., and that centrifugal separation was performed at 0° C. Twenty-seven grams of triphenylphosphine crystals was recovered, showing a recovery yeild of 90%. The crystals contained 0.1 g of triphenylphosphine oxide, and 5 mg of rhodium complex based on the weight of metallic rhodium. The mother liquid remaining after centrifugal separation contained 3 g of triphenylphosphine, 2.9 g of triphenylphosphine oxide, and 40 mg of rhodium complex based on the weight of metallic rhodium.

Reference Example 2

One hundred grams of toluene, 0.4 g of rhodium hydridocarbonyltris (triphenylphosphine) (0.045 g of metallic rhodium), 30 g of triphenylphosphine, 3 g of triphenylphosphine oxide, and 66.6 g of the compounds of formulas (I) and (II) above*3 were supplied into a 500 ml flask in a nitrogen atmosphere, and stirred to form a uniform solution. The toluene was removed from the solution by distillation, and while the distillation residue having a temperature of 120° C. was stirred in the nitrogen atmosphere, it was cooled to 10° C. and held at that temperature for 60 minutes. Then, triphenylphosphine crystals were recovered by centrifugal separation. The amount of the crystals recovered was 25.5 g, which meant a recovery yield of 85%. The crystals contained 0.1 g of triphenylphosphine oxide, and 0.04 g of rhodium hydridocarbonyltris (triphenylphosphine). The mother liquid remaining after the centrifugal separation contained 4.5 g of triphenylphosphine, 2.9 g of triphenylphosphine oxide, and 0.36 g of rhodium hydridocarbonyltris (triphenylphosphine).

*3—Compounds represented by formulas (I) and (II) when $R_1$, $R_3$ and $R_5$ are each hydrogen, and $R_2$, $R_4$ and $R_6$ are each an ethyl group.

Reference Example 3

One hundred grams of toluene, 0.46 g of rhodium hydridocarbonyltris (tri-p-tolylphosphine) (0.045 g of metallic rhodium), 30 g of tri-p-tolylphosphine, 3 g of tri-p-tolylphosphine oxide, and 66.6 g of the compounds of formulas (I) and (II) above*4 were supplied into a 500 ml flask in a nitrogen atmosphere, and stirred to form a uniform solution. The toluene was removed from the solution by distillation, and while the residue having a temperature of 120° C. was stirred in the nitrogen atmosphere, it was cooled to 10° C. and held at that temperature for 60 minutes. Then, tri-p-tolylphosphine crystals were recovered by centrifugal separation. The amount of the crystals recovered was 24 g, which meant a recovery yield of 80%. The crystals contained 0.1 g of tri-p-tolylphosphine oxide, and 0.04 g of rhodium hydridocarbonyltris (tri-p-tolylphosphine). The mother liquid remaining after the centrifugal separation contained 6 g of tri-p-tolylphosphine, 2.9 g of tri-p-tolylphosphine oxide, and 0.42 g of rhodium hydridocarbonyltris (tri-p-tolylphosphine).

*4—Compounds represented by formulas (I) and (II) when $R_1$, $R_3$ and $R_5$ are each hydrogen, and $R_2$, $R_4$ and $R_6$ are each an ethyl group.

Example 6—Recovery of Triphenylphosphine from Spent Catalyst Liquid

One hundred grams of triphenylphosphine, 0.75 liter of toluene as a solvent, and 0.15 g of rhodium acetate based on the weight of metallic rhodium were supplied into an autoclave having a capacity of 3 liters and equipped with a magnetic stirrer and a level gauge. While the internal temperature and pressure of the autoclave were maintained at 120° C. and 20 kg/cm$^2$G, respectively, propylene was introduced into the autoclave at a rate of 50 g/h through a gas blow tube, and oxo gas having a $H_2/CO$ ratio of 1 was simultaneously supplied into the autoclave through a control valve at such a rate that could maintain a constant level of the liquid in the autoclave. The unreacted gas was discharged through a purging tube, and the aldehyde formed by the reaction, toluene and a very small amount of high-boiling organic by-product, which were discharged with the unreacted gas, were cooled and collected by a cooling tube connected to the end of the purging tube.

The reaction was terminated after it was continued for 500 hours, and the reaction liquid was discharged from the autoclave. The aldehyde and a part of the high-boiling organic by-product were removed from the reaction liquid by distillation, whereby a distillation residue composed as shown in Table 4 was obtained.

TABLE 4

Composition of the distillation residue

| Constituents | Composition (wt. %) | Content in 100 g of residue (g) |
|---|---|---|
| Rhodium-triphenylphosphine complex (based on metallic rhodium) | 0.048 | 0.048 |
| Free triphenylphosphine | 30 | 30 |
| Free triphenylphosphine oxide | 1.9 | 1.9 |
| High-boiling organic by-products shown by formulas (I) and (II) above | 62 | 62 |
| Other high-boiling organic by-products | 5.5 | 5.5 |

Crystals of triphenylphosphine were recovered from 100 g of the residue by the treatment as described in Example 1. The amount of the crystals recovered was 24 g, which meant a recovery yield of 80%. The crystals contained 0.1 g of triphenylphosphine oxide, and 4.7 mg of the rhodium complex based on the weight of the metallic rhodium, so that triphenylphosphine could be selectively recovered. The mother liquid remaining after the centrifugal separation contained 6 g of triphenylphosphine, 1.8 g of triphenylphosphine oxide, and 43.3 mg of the rhodium complex based on the weight of the metallic rhodium.

Example 7—Hydroformylation of Propylene with Triphenylphosphine Purified After Recovery The procedures of Example 2 were repeated, except that 6 g of the triphenylphosphine*5 recovered in Example 6 was used after purification by recrystallization from benzene-methanol in a customary manner, and that the reaction pressure was maintained at 20 kg/cm²G. As the result, propylene showed a conversion of 99.3%, and a selectivity of 99.0% for butyraldehydes. The butyraldehydes formed by the reaction had a normal/iso ratio of 3.5. A curve showing the decrease of the oxo gas pressure in the high pressure gas holder gave a rate constant (first-order reaction) of 1.21 (l/h).
*5—A rhodium analysis confirmed that the triphenylphosphine contained virtually no rhodium complex therein.

Reference Example 4—Hydroformylation of Propylene with New Triphenylphosphine Never Used for Hydroformylation Before The procedures of Example 7 were repeated, except that the same triphenylphosphine as supplied into the autoclave in Example 6 was used instead of the triphenylphosphine recovered and purified in Example 7.

As the result, propylene showed a conversion of 99.2%, and a butyraldehyde selectivity of 99.0%. The butyraldehydes formed by the reaction had a normal/iso ratio of 3.5. The rate constant (first-order reaction) was 1.20 (l/h).

Example 8—Hydroformylation of Propylene with Triphenylphosphine Not Purified After Recovery The procedures of Example 7 were repeated, except that the triphenylphosphine recovered in Example 6 and containing a very small amount of rhodium complex was used without purification. As the result, propylene showed a conversion of 99.2%, and a butyraldehyde selectivity of 99.0%. The butyraldehydes formed by the reaction had a normal/iso ratio of 3.5, and the rate constant (first-order reaction) was 2.12 (l/h).

Example 9—Correction Experiment for Determining the Reaction Activity of Rhodium Complex Remaining in the Recovered Triphenylphosphine The procedures of Example 8 were repeated, except that no rhodium acetate was incorporated. As the result, propylene showed a conversion of 99.0%, and a butyraldehyde selectivity of 99.0%. The butyraldehyde formed by the reaction had a normal/iso ratio of 3.5. The residual rhodium complex showed a rate constant (first-order reaction) of 0.90 (l/h).

The results of Examples 7 to 9, and Reference Example 4 may be summarized as shown in Table 5 below.

TABLE 5

Activity of a rhodium complex catalyst containing 1.5 mg of metallic rhodium as initially added

| | Triphenylphosphine | Presence of rhodium | Rate constant (first-order, l/h) |
|---|---|---|---|
| Example 7 | Recovered and purified | No | 1.21 |
| Reference Example 4 | Same as used in Example 6 | No | 1.20 |
| Examples 8 and 9 | Recovered, but not purified | Yes | 1.22 (=2.12−0.90) |

It is evident from Tables 3 and 5 above that the triphenylphosphine recovered by crystallization can be recirculated directly into the reaction system for hydroformylation to produce desired results and rates of reaction. Of course, it is obvious that the purification of such triphenylphosphine after recovery does not present any problem at all.

What is claimed is:

1. In a process for the hydroformylation of an olefin comprising reacting the olefin with carbon monoxide and hydrogen in a catalyst liquid containing a Group VIII noble metal-triarylphosphine complex as a catalyst, excess triarylphosphine and an organic solvent in a reaction zone to thereby form an aldehyde, and separating the aldehyde by evaporation from said reaction zone or by distillation in a separating step, the improvement which comprises:
removing a part of said catalyst liquid from said reaction zone or said separating step as a spent catalyst liquid containing a Group VIII nobel metal-triarylphosphine complex, free triarylphosphine, triarylphosphine oxide, and, high-boiling organic by-products;
cooling said spent catalyst liquid to selectively crystallize said free triarylphosphine;
separating the crystals of said triarylphosphine from said spent catalyst liquid; and,
recycling said separated triarylphosphine to the reaction zone.

2. A process as set forth in claim 1, wherein said Group VIII noble metal is rhodium.

3. A process as set forth in claim 1, wherein said triarylphosphine is triphenylphosphine.

4. A process as set forth in claims 1, 2 or 3, wherein said aldehyde is separated by evaporation from said reaction zone.

5. A process as set forth in claim 4, wherein said aldehyde is separated from said reaction zone by stripping with an unreacted gas containing the olefin, carbon monoxide and hydrogen.

6. A process as set forth in claims 1, 2 or 3, wherein said aldehyde is separated by distillation in the separating step.

7. A process as set forth in claim 6, wherein said spent catalyst liquid removed from said separating step is distilled to remove at least a part of said solvent before said crystallization is effected.

8. A process as set forth in claim 1, wherein said spent catalyst liquid to be subjected to crystallization contains 1 to 60% by weight of triarylphosphine.

9. A process as set forth in claims 1 or 8, wherein said crystallization is effected at a temperature ranging from −78° C. to 80° C.

10. A process as set forth in claims 1 or 8, further comprising purifying said recovered triarylphosphine before recirculating it into said reaction zone.

11. A process as set forth in claim 9, further comprising purifying said recovered triarylphosphine before recirculating it into said reaction zone.

12. The process of claim 1 wherein the spent catalyst liquid subjected said cooling contains said free triarylphosphine and said high boiling organic by-products in a weight ratio in the range of 1:0.2 to 1:100.

13. The process of claim 12 wherein said weight ratio is in the range of 1:0.6 to 1:99.

14. A process as set forth in claims 12 or 13 further comprising concentrating the removed spent catalyst liquid to adjust said weight ratio to a value in said range prior to said cooling.

15. A process as set forth in claim 12 or 13 further comprising adding an additional amount of said high-boiling organic by-product to the removed spent catalyst liquid to adjust said weight ratio to a value in said range prior to said cooling.

* * * * *